United States Patent [19]

Findeisen et al.

[11] 4,238,412

[45] Dec. 9, 1980

[54] PROCESS FOR THE PREPARATION OF ACYL CYANIDES

[75] Inventors: Kurt Findeisen, Odenthal; Herbert Schwarz, Leverkusen, both of Fed. Rep. of Germany

[73] Assignee: Bayer Aktiengesellschaft, Leverkusen, Fed. Rep. of Germany

[21] Appl. No.: 967,934

[22] Filed: Dec. 8, 1978

Related U.S. Application Data

[63] Continuation of Ser. No. 777,287, Mar. 11, 1977, abandoned.

[30] Foreign Application Priority Data

Apr. 2, 1976 [DE] Fed. Rep. of Germany ....... 2614241

[51] Int. Cl.³ ............................................ C07C 120/00
[52] U.S. Cl. ......................... 260/545 R; 260/326.5 J; 260/347.8; 260/464; 260/465 R; 260/465.1; 544/8; 544/88; 544/63; 544/106; 546/184; 546/245; 546/314; 548/128; 548/215; 548/240; 548/255; 548/335; 548/337; 548/338; 548/339; 548/346; 548/262; 548/373; 548/375
[58] Field of Search ............... 260/545, 347.8, 326.5 J, 260/307 H, 307 R, 307 D, 308 R, 308 A, 308 B, 464, 465 R, 465.1; 544/106; 548/335, 337, 338, 339, 373, 375, 377, 378; 560/155, 19, 125

[56] References Cited

U.S. PATENT DOCUMENTS 4,117,008 9/1978 Klenk et al. .................... 260/545 R

OTHER PUBLICATIONS

Erlenmeyer, Liebigs Ann. Chem. vol. 287, pp. 302–307 (1895).
Thesing et al., Angewandte Chemie, vol. 68, pp. 425–426, 434–435, (1956).

Primary Examiner—Howard T. Mars
Attorney, Agent, or Firm—Sprung, Felfe, Horn, Lynch & Kramer

[57] ABSTRACT

Acyl cyanides of the general formula

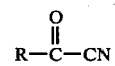

in which
R represents alkyl or substituted alkyl of from 1 to 8 carbon atoms; cycloalkyl or substituted cycloalkyl with 3 to 12 carbon atoms; aryl or substituted aryl; or an optionally substituted 5-membered or 6-membered heterocyclic radical which can additionally also be fused with a benzene ring, are prepared by reacting the corresponding carboxylic acid anhydride with an alkali metal cyanide or anhydrous hydrocyanic acid, at a temperature of between 50° and 250° C. and the resulting acyl cyanide is removed from the reaction medium by distillation, immediately after it has been formed.

23 Claims, No Drawings

PROCESS FOR THE PREPARATION OF ACYL CYANIDES

This is a continuation of application Ser. No. 777,287, filed Mar. 11, 1977, now abandoned.

The present invention relates to a process for the preparation of certain acyl cyanides. Such compounds are useful as starting materials for the synthesis of herbicides.

It is known that acyl cyanides can be prepared by reacting acyl halides with metal cyanides (see Angew. Chem 68, 425–448 (1956)). However, this process has a number of disadvantages. Thus, for example, it is expensive and can be carried out technically only with difficulty since it is a two-phase reaction in which a solid is reacted with a liquid or with a substance present in solution. Moreover, the reaction does not give a single reaction product but a mixture of substances which is difficult to separate and which also contains, in addition to the particular acyl cyanide, a relatively large amount of a corresponding dimer. Accordingly, the yields of the acyl cyanide are relatively low. A further disadvantage of this process is that the washing water obtained during working up has to be subjected to thorough purification before it is run off since it still contains considerable amounts of highly toxic metal cyanides which are used in excess during the reaction.

Furthermore, it is known that aroyl cyanides can be synthesized by reacting arylcarboxylic acid chlorides with hydrocyanic acid, in the presence of pyridine as an acid-binding agent, in absolute ether (see Angew. Chem. 68, 425–448 (1956)). However, this process also is associated with several disadvantages. Thus firstly, it is not generally applicable. Moreover, it is technically very involved because the operations with pyridine, which is highly toxic, and with ether, which is readily inflammable, demand particularly stringent safety precautions. Moreover, in this case also through purification of the washing water obtained during working up is unavoidable because of the pyridine dissolved therein. The fact that a considerable amount of dimeric aroyl cyanide is formed during the reaction is also a disadvantage since, as a result of this, both the yield of aroyl cyanide is greatly reduced and the isolation thereof is made more difficult.

It is also known to react benzoic acid anhydride with potassium cyanide in an equivalent amount and this reaction gives benzoyl cyanide in a low yield (about 10% of theory) (Liebigs Annalen der Chemie 287, page 306 (1895)). The benzoyl cyanide must be removed with ether from the viscous, very highly resinified, dark brown mass which is formed as the main product. This process is technically completely unsuitable, since not only the extraction with ether leads to difficulties which cannot be overcome technically but there is also no further use for the very highly resinified dark brown masses. This method is, therefore, merely a possible means of forming benzoyl cyanide.

The present invention now provides a process for the preparation of an acyl cyanide of the general formula

in which
R represents alkyl or substituted alkyl of from 1 to 8 carbon atoms; cycloalkyl or substituted cycloalkyl with 3 to 12 carbon atoms; aryl or substituted aryl; or an optionally substituted 5-membered or 6-membered heterocyclic radical which can additionally also be fused with a benzene ring, in which a carboxylic acid anhydride of the general formula

in which
R has the above-mentioned meaning,
is reacted with an alkali metal cyanide or anhydrous hydrocyanic acid, optionally in the presence of a diluent, at a temperature of between 50° and 250° C. and the resulting acyl cyanides (I) are removed from the reaction medium by distillation, if appropriate under reduced pressure, immediately after they have formed.

Preferably, R represents straight-chain or branched alkyl with 1 to 4 carbon atoms, which can optionally carry one or more substituents selected from alkoxy with 1 to 4 carbon atoms, carbalkoxy with 1 to 4 carbon atoms in the alkoxy group, nitro, nitrile and halogen (namely fluorine, chlorine, bromine or iodine); cycloalkyl with 5 or 6 carbon atoms in the ring system and which optionally carries one or more substituents selected from alkyl with 1 to 4 carbon atoms, alkoxy or carbalkoxy with, in either case, up to 4 carbon atoms in the alkyl part, nitro, nitrile and halogen (for example fluorine, chlorine and bromine); phenyl or naphthyl, either of which optionally carries one or more substituents selected from alkyl with 1 to 4 carbon atoms, alkoxy or carbalkoxy with, in either case, up to 4 carbon atoms in the alkyl part, nitro and halogen (for example fluorine, chlorine and bromine); or a 5-membered or 6-membered heterocyclic radical which can contain 1 to 3 hetero-atoms, selected from oxygen, sulphur and nitrogen, in the ring and which can optionally carry one or more substituents selected from alkyl with 1 to 4 carbon atoms, alkoxy or carbalkoxy with, in either case, up to 4 carbon atoms in the alkyl part, nitro, nitrile and halogen (for example fluorine, chlorine and bromine) and can optionally be fused with a benzene ring.

Examples which may be mentioned of the heterocyclic radicals R are morpholinyl, imidazolyl, pyrazolyl, pyrrolyl, isoxazolyl, piperidinyl, oxazolyl, 1,2,4-triazol-1-yl, 1,2,4-triazol-4-yl, 1,2,3-triazolyl, 1,2,4-thiadiazol-2-yl, benzimidazolyl and furanyl.

It is to be regarded as extremely surprising that acyl cyanides of the formula (I) are accessible in high yield and excellent purity by the process according to the invention since, in view of the known state of the art, it was to be expected that either the same difficulties would arise with this process as in the case of the reaction of acyl halides with alkali metal cyanides or heavy metal cyanides in a two-phase system or that the desired acyl cyanide would be formed only in traces. In particular, it was in no way to be foreseen that the formation of undesired dimeric acyl cyanides or resinous products would not take place at all.

The process according to the invention has a number of advantages. Thus, it is not restricted to the synthesis of a few specific compounds but has very broad application. Furthermore, the process according to the invention can give acyl cyanides in virtually quantitative yield and excellent purity, free from by-products which are troublesome or pollute the environment.

An additional important advantage of the process according to the invention is that working up presents no problems. The alkali metal salts of the carboxylic acids which are formed in the course of the reaction are separated off, for example by filtration, and the filtrate can be distilled or used direct for a further reaction. Furthermore, the alkali metal salts of the carboxylic acids which are formed from the acid anhydrides (II) in the course of the reaction can be reconverted into the anhydrides. If hydrocyanic acid is used in place of the alkali metal cyanides, benzoic acid is formed as the by-product and this can be put to diverse further use in chemistry. The process according to the invention is thus a valuable enrichment of the art.

If benzoic acid anhydride and anhydrous hydrocyanic acid are used as the starting materials, the course of the reaction can be represented by the following equation.

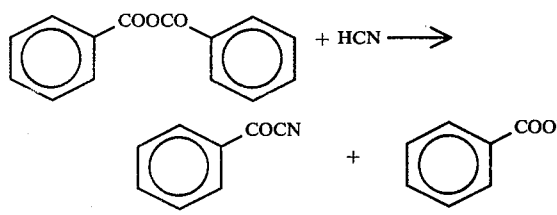

When benzoic acid anhydride and sodium cyanide are used, the course of the reaction can be represented by the following equation:

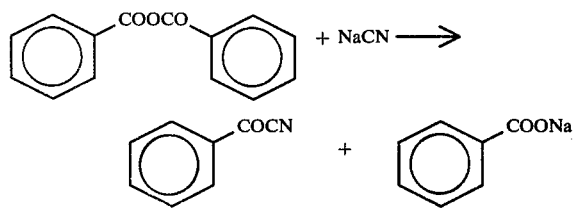

The acid anhydrides generally defined by the formula (II) can be prepared by known processes.

Preferred examples of acid anhydrides of the formula (II) which may be mentioned are: acetic anhydride, propionic anhydride, pivalic anhydride, cyclohexanecarboxylic acid anhydride, benzoic acid anhydride, m-chlorobenzoic acid anhydride, 3,5-dichlorobenzoic acid anhydride, naphthalene-1-carboxylic acid anhydride and 1-phenyl-5-pyrazolone-3-carboxylic acid anhydride. Particularly preferred anhydrides which may be mentioned are the aromatic carboxylic acid anhydrides, especially benzoic acid anhydride.

Particularly preferred alkali metal cyanides which may be mentioned are sodium cyanide and potassium cyanide.

Possible diluents which can be employed when carrying out the process according to the invention are all inert organic solvents which do not enter into a chemical reaction with either the carboxylic acid anhydrides, or the metal cyanides or hydrocyanic acid. Examples of such solvents are the xylenes, such as o-xylene, chlorobenzene, o-dichlorobenzene, the trichlorobenzenes, nitrobenzene and tetramethylenesulphone. An excess of the carboxylic acid anhydride (II) is particularly suitable as a diluent. In principle, however, it is also possible to carry out the reaction according to the invention without diluents.

The reaction temperature can be varied within a fairly wide range. In general, the reaction is carried out at temperatures of between 50° and 250° C. and preferably of between 100° and 230° C.

The reaction is generally carried out under normal pressure. When low-boiling aliphatic carboxylic acid anhydrides are used, however, a slight excess pressure is advantageous and the excess pressure is then, in general, from 1 to 10, and preferably from 1 to 5, atmospheres. In order to distill off the acyl cyanides formed, on the other hand, it can be advantageous to work under reduced pressure, in the range of 750 to 0.05 mm Hg, the most advantageous pressure being determined by the desired acyl cyanide and the temperature employed.

The reaction can be accelerated by adding catalytic amounts of a base or Lewis acid. Examples of suitable bases are tertiary amines, such as dimethylbenzylamine and 1,4-diazabicyclo[2.2.2] octane, and alkali metal salts of carboxylic acids, for example sodium benzoate. Examples of suitable Lewis acids which may be mentioned are zinc chloride, zinc cyanide, copper(I) cyanide and copper(II) cyanide, as well as $Na_3[Cu(CN)_4]$.

When carrying out the process according to the invention, in general stoichiometric amounts of the acid anhydride are reacted with an alkali metal cyanide or anhydrous hydrocyanic acid. However, the acid anhydride can also be used in excess and in that case is advantageously even used as the solvent.

Working up is carried out after the reaction has ended, usually by distillation and, where appropriate, recrystallisation.

The mixture of the acid anhydride and hydrocyanic acid can also be reacted, according to the invention, in the gas phase, without the special use of catalysts.

The acyl cyanides of the formula (I) which can be prepared by the process according to the invention are valuable starting materials, for example for the synthesis of 1,2,4-triazin-5-ones, which possess outstanding herbicidal properties (see German Offenlegungsschrift (German Published Specification) 2,224,161).

Thus, for example, 3-methyl-4-amino-6-phenyl-1,2,4-triazin-5-one of the formula

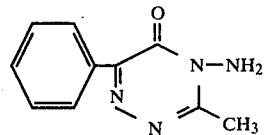

can be prepared by reacting benzoyl cyanide, in the presence of concentrated hydrochloric acid, with ethanol in a first stage and, in a second stage, reacting the resulting phenylglyoxylic acid ethyl ester with acetylhydrazine, whereupon 1-phenylglyoxylic acid ethyl ester-2-acetylhydrazine is formed, which, in a third stage, is converted, with hydrazine hydrate, in the presence of pyridine, into the abovementioned end product. This multi-stage synthesis can be represented by the following equations:

1st stage:

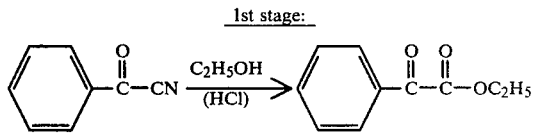

-continued
2nd stage:

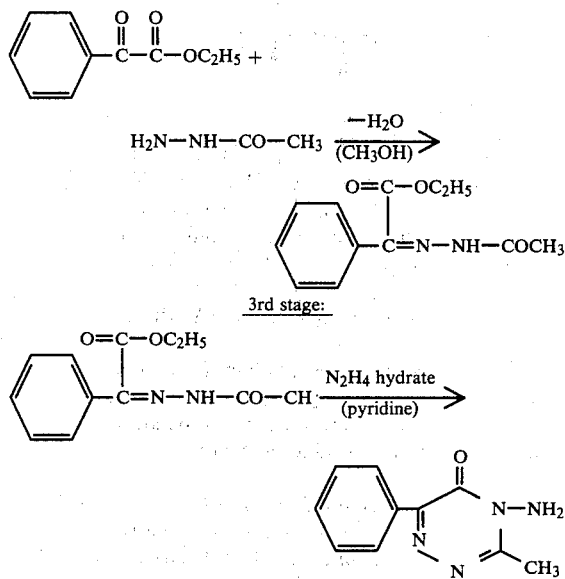

The process according to the invention is illustrated by the preparative Examples which follow:

EXAMPLE 1

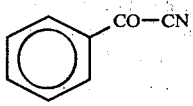   (1)

Process variant A:

1,130 g (5 mol) of benzoic acid anhydride were heated to 180° C. in a 2 liter four-necked flask fitted with a stirrer, a thermometer, a reflux condenser and a dropping funnel and 200 ml (5 mol) of anhydrous hydrocyanic acid were added dropwise in the course of 5 hours. The hydrocyanic acid which was not converted immediately was recycled back into the reaction vessel by cooling. After the reaction had ended, the mixture was subjected to fractional distillation.

Yield: 630 g (96% of theory) of benzoyl cyanide with a melting point of 31° C.

Benzoic acid, which was formed quantitatively as a by-product, was converted into benzoic acid anhydride by known methods.

Process variant B:

1,130 g (5 mol) of benzoic acid anhydride and 250 g (5 mol) of 98% pure sodium cyanide were mixed.

The reaction vessel used was a 3 liter glass beaker with ground flange provided with a peripheral helical ribbon impeller, a thermometer, a column head and a distillation bridge. The mixture of benzoic acid anhydride and sodium cyanide could be stirred easily at 50° C. The mixture was warmed to 150° C. under a water-pump vacuum (about 15 mm Hg) in the course of 30 minutes. After 15 minutes, the temperature was raised to 160°–170° C. The benzoyl cyanide formed distilled over at a temperature of 105°–125° C. After about 2–2.5 hours, the internal temperature was raised to 190°–200° C. The remaining benzoyl cyanide then distilled over.

Yield: 650 g (99% of theory) of benzoyl cyanide with a melting point of 31° C.

Process variant C:

452 g (2 mol) of benzoic acid anhydride were added to 160 ml of anhydrous hydrocyanic acid and the mixture was charged slowly through a tube, which was heated to 250° C. and filled with Raschig rings, and collected in a receiver.

After fractional distillation, during which the excess hydrocyanic acid was recovered, 236 g (90% of theory) of benzoyl cyanide with a melting point of 31° C. were obtained in addition to benzoic acid and a little unconverted benzoic acid anhydride.

Process variant D:

904 g (4 mol) of benzoic acid anhydride and 98 g (2 mol) of sodium cyanide were mixed in a three-necked flask and slowly warmed to 200° C. in vacuo, whereupon the reaction product distilled off continuously in vacuo (14 mm Hg). The residue remained readily stirrable down to 40° C. and could be used immediately in order to prepare benzoic acid anhydride from the sodium benzoate formed.

Yield: 130 g (99% of theory, relative to the sodium cyanide employed) of benzoyl cyanide.

EXAMPLE 2

93 g (0.5 mol) of pivalic anhydride were mixed with 24.5 g (0.5 mol) of sodium cyanide and the mixture was slowly warmed in vacuo (15 mm Hg). The reaction product formed was distilled off direct and then fractionated.

Yield: 39.4 g (71% of theory) of pivaloyl cyanide, boiling point 48°–54° C./15 mm Hg.

EXAMPLE 3

295 g (1 mol) of 3-chloro-benzoic acid anhydride were mixed with 65 g of potassium cyanide in a 750 ml three-necked flask and the mixture was slowly warmed to 230° C. in the course of 120 minutes. The reaction product was removed from the Na salt of 3-chlorobenzoic acid by applying a vacuum. The fractional distillation gave 160 g (97% of theory) of 3-chlorobenzoyl cyanide; boiling point 118°–120° C. under 14 mm Hg; melting point 146°–148° C. (from wash benzine).

EXAMPLE 4

105.3 g (0.33 mol) of 4-nitrobenzoic acid anhydride were mixed with 16.3 g (0.33 mol) of sodium cyanide in a 400 ml flask and the mixture was warmed slowly to 230° C. in vacuo, whereupon 55.4 g (94% of theory) of 4-nitrobenzoyl cyanide distilled off; boiling point 116°–118° C. under 0.1 mm Hg.

EXAMPLE 5

264 (1 mol) of 2,5-dichloro-benzoic acid anhydride and 49 g (1 mol) of sodium cyanide were heated in the course of 2 hours, in vacuo, to 200° C. in a 500 ml flask which was fitted with a stirrer and a distillation apparatus. As the temperature rose, 2,5-dichlorobenzoyl cyanide distilled at a rapid rate into the receiver.

Fractional distillation gave: 194 g (97% of theory) of 2,5-dichlorobenzoyl cyanide; boiling point 140°–142° C. under 12 mm Hg; melting point 63°–65° C. (from wash benzine).

EXAMPLE 6

127 g (0.5 mol) of 4-methyl-benzoic acid anhydride were warmed to 185°–190° C. in a 250 ml three-necked flask fitted with a stirrer, a cooled dropping funnel and a reflux condenser and 20 ml (0.5 mol) of anhydrous hydrocyanic acid were added dropwise in the course of 2 hours. The reaction product was distilled off continuously.

Yield: 67.5 g (93% of theory) of 4-methyl-benzoyl cyanide; boiling point 112°–114° C. under 14 mm Hg; melting point 50°–52° C. (from wash benzine).

EXAMPLE 7

In the manner described in Example 5, 163 g (0.5 mol) of 1-naphthalenecarboxylic acid anhydride and 25 g (0.5 mol) of sodium cyanide were heated to 200° C. in the course of 3 hours, whereupon 1-naphthalenecarboxylic acid cyanide distilled off. After a further distillation in order to separate off entrained traces of the starting materials, 84 g (93% of theory) of 1-naphthalenecarboxylic acid cyanide were obtained; boiling point 117°–119° C. under 0.08 mm Hg; melting point 100°–102° C. (from wash benzine).

EXAMPLE 8

In the manner described in Example 3, 295 g (1 mol) of 4-chlorobenzoic acid anhydride and 49 g (1 mol) of sodium cyanide were warmed in the course of 2 hours to 210° C. in a three-necked flask. During the slightly exothermic reaction, the reaction product formed was distilled off in vacuo (13 mm Hg). Yield: 158 g (96% of theory) of 4-chloro-benzoyl cyanide; boiling point 114°–116° C. under 13 mm Hg.

EXAMPLE 9

In the manner described in Example 5, 286 g (1 mol) of p-methylbenzoic acid anhydride and 65 g (1 mol) of potassium cyanide were warmed to 190° C. in the course of 2 hours. The p-methoxybenzoyl cyanide that collected in the distillation receiver was obtained in a vary pure form. Yield: 151 g (94% of theory) of p-methoxybenzoyl cyanide.

It will be understood that the specification and examples are illustrative but not limitative of the present invention and that other embodiments within the spirit and scope of the invention will suggest themselves to those skilled in the art.

What is claimed is:

1. A process for the preparation of an acyl cyanide of the general formula

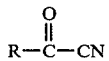

in which
R represents alkyl or substituted alkyl of from 1 to 8 carbon atoms, wherein the substituents are selected from alkoxy or carbalkoxy of up to 4 carbon atoms in the alkoxy moiety, nitro, nitrile and halo; cycloalkyl or substituted cycloalkyl with 3 to 12 carbon atoms wherein the substituent is selected from alkyl, alkoxy and carbalkoxy of up to 4 carbon atoms in each alkyl moiety, nitro, nitrile and halo; aryl or substituted aryl wherein the substituents are selected from alkyl, alkoxy and carbalkoxy of up to 4 carbon atoms in the alkyl moiety, nitro and halo; or an optionally substituted 5-membered or 6-membered heterocyclic radical which can additionally also be fused with a benzene ring, wherein said substituents are selected from alkyl, alkoxy and carbalkoxy of up to 4 carbon atoms in each alkyl moiety, nitro, nitrile and halo;

which process comprises reacting a carboxylic acid anhydride of the general formula

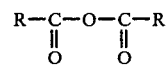

in which
R has the above meaning with an alkali metal cyanide, at a temperature of between 50° C. and 250° C. under vacuum and the resulting acyl cyanide is removed from the reaction medium by distillation under vacuum, immediately after it has been formed.

2. A process as claimed in claim 1 wherein R is alkyl of up to 4 carbon atoms.

3. A process as claimed in claim 1 wherein R is substituted alkyl wherein the substituents are selected from alkoxy of up to 4 carbon atoms, carbalkoxy of up to 4 carbon atoms in the alkoxy group, nitro, nitrile and halogen.

4. A process as claimed in claim 1 wherein R is cycloalkyl of from 5 or 6 carbon atoms in the ring.

5. A process as claimed in claim 1 wherein R is substituted cycloalkyl of from 5 or 6 carbon atoms in the ring wherein the substituents are selected from alkyl of up to 4 carbon atoms, alkoxy or carbalkoxy of up to 4 carbon atoms in the alkyl part, nitro, nitrile and halogen.

6. A process as claimed in claim 1 wherein R is phenyl or naphthyl.

7. A process as claimed in claim 1 wherein R is substituted phenyl or naphthyl wherein the substituents are selected from alkyl of up to 4 carbon atoms, alkoxy or carbalkoxy of up to 4 carbon atoms in the alkyl part, nitrogen and halogen.

8. A process as claimed in claim 1 wherein R is a heterocyclic radical selected from morpholinyl, imidazolyl, pyrazolyl, pyrrolyl, isoxazolyl, piperidinyl, oxazolyl, 1,2,4-triazol-1-yl, 1,2,4-triazol-4-yl, 1,2,3-triazolyl, 1,2,4-thiadiazol-2-yl, benzimidazolyl and furanyl.

9. A process as claimed in claim 1 wherein R represents straight-chain or branched alkyl of up to 4 carbon atoms, or substituted alkyl of up to 4 carbon atoms wherein one or more substituents are selected from alkoxy of up to 4 carbon atoms, carbalkoxy of up to 4 carbon atoms in the alkoxy group, nitro, nitrile and halogen; cycloalkyl of from 5 or 6 carbon atoms in the ring system or substituted cycloalkyl of from 5 or 6 carbon atoms in the ring wherein one or more substituents are selected from alkyl of up to 4 carbon atoms, alkoxy or carbalkoxy of up to 4 carbon atoms in the alkyl part, nitro, nitrile and halogen; phenyl or naphthyl, or substituted phenyl or naphthyl substituted by one or more substituents selected from alkyl of up to 4 carbon atoms, alkoxy or carbalkoxy of up to 4 carbon atoms in the alkyl part, nitro and halogen; or a 5-membered or 6-membered heterocyclic radical which can contain 1 to 3 hetero-atoms, selected from oxygen, sulphur and nitrogen, in the ring, or a substituted 5-membered or 6-membered heterocyclic radical wherein one or more substituents are selected from alkyl of up to 4 carbon atoms, alkoxy or carbalkoxy of up to 4 carbon atoms in the alkyl part, nitro, nitrile and halogen and can optionally be fused with a benzene ring.

10. A process as claimed in claim 1 wherein the reaction is carried out at a temperature of between 100° and 230° C.

11. A process as claimed in claim 1 wherein the carboxylic acid anhydride (II) is an aromatic carboxylic acid anhydride.

12. A process as claimed in claim 11 wherein the carboxylic acid anhydride (II) is an aralkyl acid anhydride.

13. A process as claimed in claim 1 wherein the alkali metal cyanide is sodium or potassium cyanide.

14. A process as claimed in claim 1 wherein excess carboxylic acid anhydride is employed as a diluent.

15. A process as claimed in claim 1 wherein the reaction is effected in the presence of an organic solvent that is inert to the reactants.

16. A process as claimed in claim 1 wherein the reaction is effected in the presence, as a catalyst, of a base or of a Lewis acid.

17. A process as claimed in claim 16 wherein the catalyst is a tertiary amine, zinc chloride, zinc cyanide or copper(I) cyanide.

18. A process as claimed in claim 1 wherein the acyl cyanide formed is removed from the reaction mixture by distillation under reduced pressure.

19. A process as claimed in claim 1 wherein said acyl cyanide is benzoyl cyanide and the carboxylic acid anhydride is benzoic acid anhydride.

20. A process as claimed in claim 1 wherein said acyl cyanide is pivaloyl cyanide and the carboxylic acid anhydride is pivalic anhydride.

21. A process as claimed in claim 1 wherein said acyl cyanide is 3-chlorobenzoyl cyanide and said carboxylic acid anhydride is 3-chlorobenzoic acid anhydride.

22. A process as claimed in claim 1 wherein said acyl cyanide is 2,5-dichlorobenzoyl cyanide and said carboxylic acid anhydride is 2,5-dichlorobenzoic acid anhydride.

23. A process as claimed in claim 1 wherein said acyl cyanide is 4-methyl-benzoyl cyanide and said carboxylic acid anhydride is 4-methyl benzoic acid anhydride.

* * * * *